US 6,190,367 B1

(12) United States Patent
Hall

(10) Patent No.: US 6,190,367 B1
(45) Date of Patent: Feb. 20, 2001

(54) MEDICAL SITE PREP DEVICE

(75) Inventor: John P. Hall, Raleigh, NC (US)

(73) Assignee: Becton, Dickinson and Company, Franklin Lakes, NJ (US)

(*) Notice: Under 35 U.S.C. 154(b), the term of this patent shall be extended for 0 days.

(21) Appl. No.: 09/401,115

(22) Filed: Sep. 22, 1999

(51) Int. Cl.[7] ................................................. A61M 35/00
(52) U.S. Cl. .......................... 604/290; 604/310; 604/311; 604/181
(58) Field of Search ................................ 604/290, 19, 2, 604/3, 289, 310, 311, 306, 87, 181, 182, 185, 212, 218; D24/119

(56) References Cited

U.S. PATENT DOCUMENTS

| 3,324,855 | * | 6/1967 | Heimlich. | |
| 3,495,917 | * | 2/1970 | Truhan. | |
| 3,520,300 | * | 7/1970 | Flower. | |
| 3,580,254 | * | 5/1971 | Stuart | 604/290 |
| 3,964,482 | | 6/1976 | Gerstel et al. | 128/260 |
| 4,415,288 | * | 11/1983 | Gordon et al. | 401/132 |
| 4,498,796 | * | 2/1985 | Gordon et al. | 401/132 |
| 4,693,711 | * | 9/1987 | Bremer et al. | 604/306 |
| 4,943,274 | * | 7/1990 | Edwards | 604/2 |
| 5,250,023 | | 10/1993 | Lee et al. | 604/20 |
| 5,655,258 | * | 8/1997 | Heintz | 15/415.1 |

FOREIGN PATENT DOCUMENTS

| 0 429 842 A2 | 6/1991 | (EP) | A61N/1/30 |
| WO 96/17648 | 6/1996 | (WO) | A61N/1/30 |
| WO 96/37256 | 11/1996 | (WO) | A61N/1/30 |
| WO 99/03521 | 1/1999 | (WO) | A61M/5/30 |

* cited by examiner

Primary Examiner—Sharon Kennedy
Assistant Examiner—Kevin C. Sirmons
(74) Attorney, Agent, or Firm—Eric M. Lee, Esq.

(57) ABSTRACT

The medical site prep device of this invention includes a main body portion, preferably in the shape of a hollow ring, a sponge-like material attached to the bottom of the main body portion, a plate disposed in the center of the main body portion and a piston disposed above the plate in the center of the main body portion. The medical site prep device of this invention can simultaneously dispense an anti-microbial agent and a topical anesthetic at the medical site on a patient.

6 Claims, 6 Drawing Sheets

MEDICAL SITE PREP DEVICE

FIELD OF THE INVENTION

This invention relates to a device for applying medications topically to a surgical or other medical site on a patient. More specifically, this invention relates to a medical device that can topically apply both an anti-microbial agent and an anesthetic agent to a medical site on a patient.

BACKGROUND OF THE INVENTION

In many medical procedures, a needle is used to penetrate the patient's skin to either inject medicaments or other fluids into the patient or to withdraw blood from a patient. For example, a hypodermic syringe may be used to inoculate a patient or to administer other drugs to a patient, a blood collection set having a blood collection needle attached thereto may be inserted into a patient's vasculature to obtain a blood sample from the patient, or an intravenous (IV) catheter may be inserted into a patient's vasculature via an introducer needle to provide continued access to a patient's vasculature for the administration of various fluids or medicaments to the patient. Other medical procedures requiring the use of a needle include sewing broken skin together to facilitate the repair of the skin after a major cut in the skin. In addition to needles that penetrate a patient's skin, a sharp scalpel may be used in other medical procedures to cut the skin so a physician can remove unwanted tissue or to provide access to a portion of the patient's body below the skin.

The skin acts as a barrier to prevent microorganisms from entering the body of the patient. Typically the skin contains a multiplicity of microorganisms thereon. As long as the skin surface is intact, the microorganisms generally present no problem to the patient. However, when a medical procedure is performed on a patient, such as one of the procedures decribed above, the natural barrier formed by the skin is breached providing a pathway for microorganisms to enter the body. Such microorganisms can cause serious infection to a patient and, if left untreated, could result in death to the patient. Thus it is important to prevent these microorganisms from entering the body. Various protocols to reduce or eliminate skin microorganisms have been developed and are generally practiced rigorously prior to the performance of any of the medical procedures outlined above. The protocols generally involve a thorough swabbing of the skin surface with an appropriate antimicrobial agent such as isopropyl alcohol, an iodophor or polyvinylpyrrolidone iodine.

In addition to the need to prevent the ingress of microorganisms into the body via an opening in the skin created during a medical procedure, maintaining patient comfort during a medical procedure is also a legitimate concern for the caregiver. All of the medical procedures outlined above can be performed without the use of an anesthetic. However, these procedures can be uncomfortable and even quite painful to the patient. Various anesthetic compositions are available and are typically delivered to the patient via a hypodermic syringe. Obviously, for patients who feel exceptional discomfort having a needle inserted into them, the use of a hypodermic needle to deliver a dose of anesthetic is undesirable.

Recently, anesthetics that can be delivered to the patient topically have become commercially available. One problem with these topical anesthetics is the time delay between application and the onset of "numbness". If the delay is too long, the medical personnel will have to waste valuable time waiting for the anesthetic to take effect before the medical procedure can begin. If the patient has to apply the anesthetic, the patient will be required to handle the anesthetic carefully to prevent contamination, and apply the anesthetic properly and to the appropriate part of the body where the medical procedure will take place. In addition, the patient will have to carefully note the time when the anesthetic is applied to ensure that the anesthetic is still effective during the entire medical procedure.

Another concern relating to such topical anesthetics is whether the effect of the anesthetic will extend significantly below the skin surface. Because the skin is an effective barrier to the entry of microorganisms into a patient's body, it is difficult to get medical agents to penetrate the skin effectively without irritating or otherwise damaging the skin. If the anesthetic does not effectively penetrate the skin, the patient would still feel discomfort or pain from certain medical procedures where a needle or scalpel penetrated the patient's body below the skin a significant distance. To remedy this problem there has been work done to identify appropriate chemical penetration enhancers to facilitate transdermal drug delivery.

Anti-microbial agents and topical anesthetics are typically applied separately with some type of cotton swab separately used to apply each substance. Unfortunately, there is currently no single device that can apply both the anti-microbial agent and the topical anesthetic to the patient. Such a device would be desireable because it would facilitate the application of both the anti-microbial agent and the topical anesthetic so the patient would enjoy the benefits of both. In addition, significant time could be saved by using a single device to apply both the anti-microbial agent and the topical anesthetic.

SUMMARY OF THE INVENTION

It is therefore an object of this invention to provide a medical device that can apply an anti-microbial agent and a topical anesthetic simultaneously.

It is another object of this invention to provide a medical device that can quickly and easily apply an anti-microbial agent and a topical anesthetic simultaneously.

It is yet another object of this invention to provide a medical device that can enhance the permeation through the skin of a topically applied anethestic composition in order to create an anesthetic effect at the site within a short time after application.

It is still another object of this invention to provide a medical device that can enhance the permeation through the skin of a topically applied anesthetic composition in order to create an anesthetic effect in the patient a signficant distance below the skin.

The medical site prep device of this invention includes a main body portion, preferably in the shape of a hollow ring having a central opening, a sponge or a sponge-like material attached to the bottom of the main body portion, a plate disposed in the central opening of the main body portion and a piston disposed above the plate in the central opening of the main body portion.

Preferably, the main body portion has an open bottom, or a bottom defining a plurality of holes therethrough, with the sponge covering the opening. An anti-microbial agent is carried in the main body portion. The anti-microbial agent may be microencapsulated or may be otherwise contained in a rupturable container membrane. The anti-microbial agent may be any antimicrobial that is generally recognized as safe ("GRAS") by the FDA and that substantially inhibits microbial growth on the skin.

Preferably the plate is formed with a plurality of lumens extending therethrough with the bottom of the plate formed with a plurality of sharpened points. An anesthetic agent is preferably carried in a rupturable pouch between the plate and the piston. The anesthetic agent may be any topically applied anesthetic that is classified as GRAS by the FDA. In order to enhance the permeation of the anesthetic agent through the skin, a permeation enhancer may also be included in the rupturable pouch containing the anesthetic agent. A movable piston is located above the rupturable pouch. If desired, the top of the plate can have sharpened points adjacent to the rupturable pouch to facilitate the rupture of the pouch when the piston is pushed down.

To use the medical site prep device, the clinician squeezes the main body portion to rupture the container holding the anti-microbial agent. Thereupon, the anti-microbial agent flows out of the main body portion and into the sponge below the main body portion. By rubbing the sponge on the patient's skin, any microorganisms on the patient's skin are killed and the area is sterilized. Next, the clinician can push the piston against the pouch containing the topical anesthetic. This motion ruptures the pouch so that the topical anesthetic flows through the lumens in the plate. In addition, by pushing the pistion down, the sharpened points at the bottom of the plate can be moved against the patient's skin to abrade the area where the topical anesthetic is applied. This enhances the permeation of the anesthetic through the skin.

BRIEF DESCRIPTION OF THE DRAWINGS

The above and other objects and advantages will be apparent upon consideration of the following drawings and detailed description. The preferred embodiments of the present invention are illustrated in the appended drawings in which like reference numbers refer to like elements and in which.

DETAILED DESCRIPTION OF THE INVENTION

Figure 5:
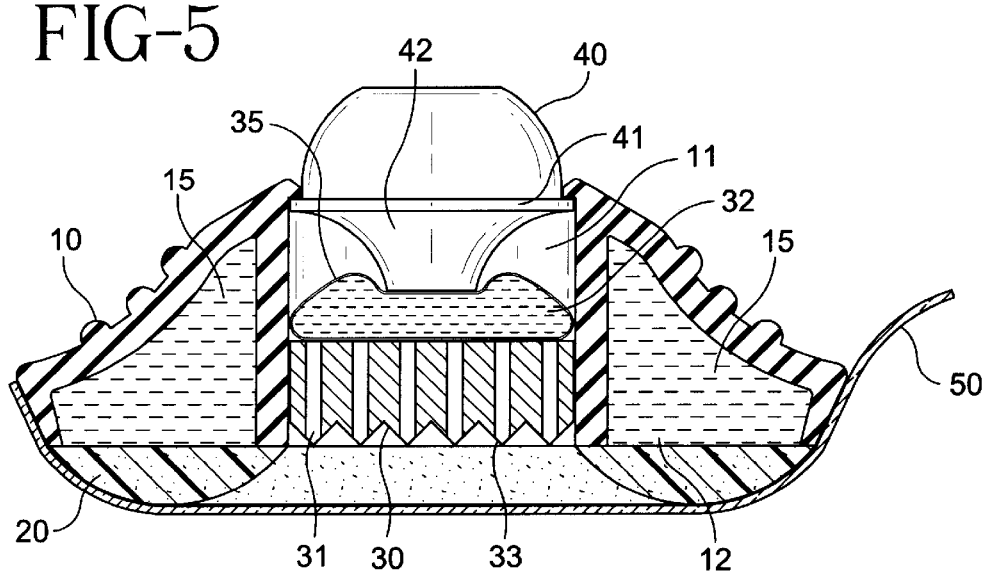
FIG. 5 is a cross-sectional view of the medical site prep device of this invention prior to use.
Figure 6:
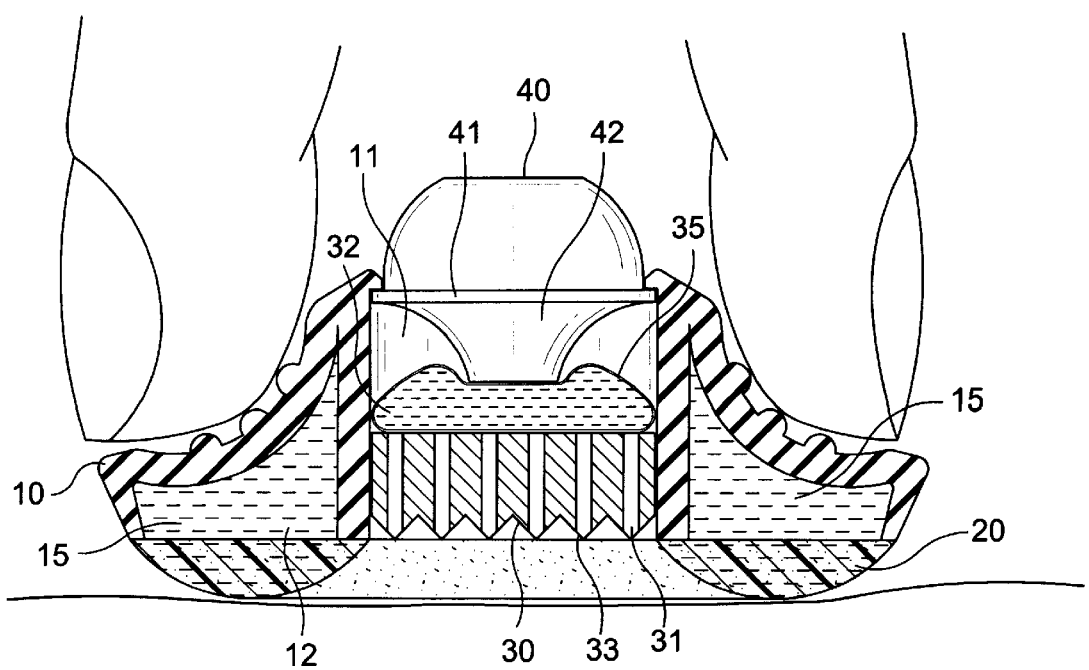
FIG. 6 is a cross-sectional view of the medical site prep device of this invention showing a clinician applying the anti-microbial agent to a patient's skin.
Figure 7:
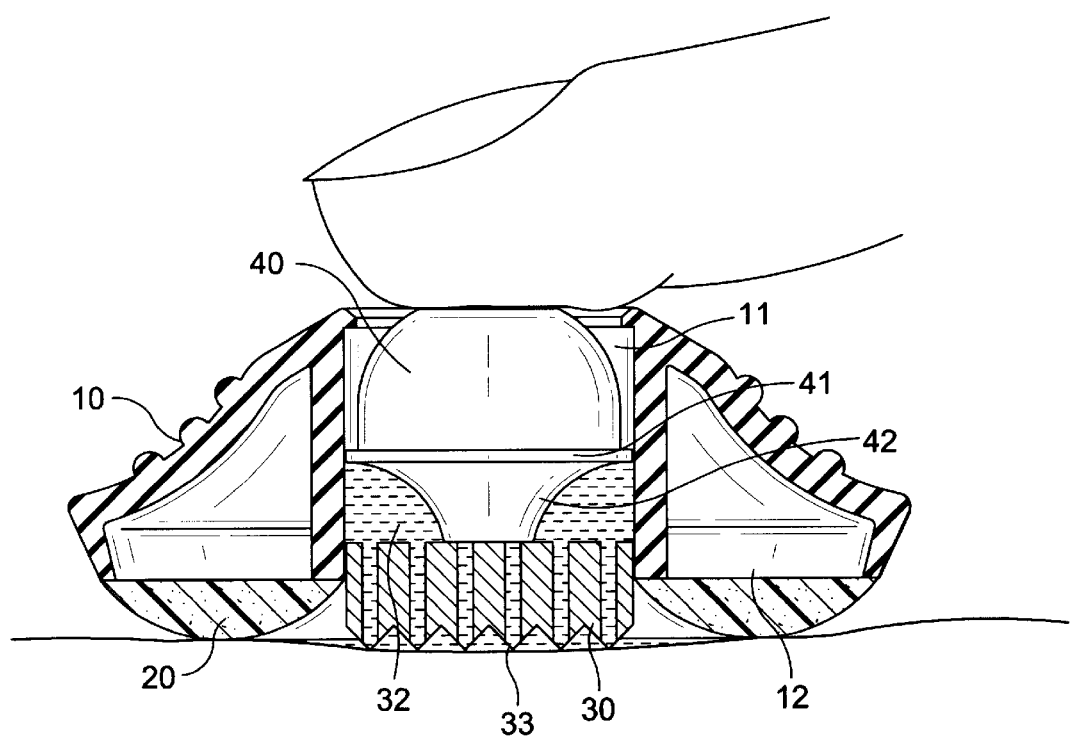
FIG. 7 is a cross-sectional view of the medical site prep device of this invention showing a clinician pushing the piston to apply the topical anesthetic to a patient's skin.

As used herein "top" and "above" means a position on the medical site prep device that is toward the top of the device as seen in FIGS. 5–7, while "bottom" and "below" means a position on the medical site prep device that is toward the bottom of the device as seen in FIGS. 5–7. As used herein "distal" means a position toward the patient and away from the clinician using the medical site prep device, while "proximal" means a position away from the patient and toward the clinician.

The medical site prep device of this invention includes a main body portion 10, preferably in the shape of a hollow ring, a sponge 20 attached to the bottom of main body portion 10, a plate 30 disposed in the center of main body portion 10 and a piston 40 disposed above plate 30 in the center of main body portion 10. A removable film 50 is disposed over sponge 20 to maintain the sterility of the device prior to use.

Main body portion 10 is molded from a durable yet flexible material such as a thermoplastic elastomer. Main body portion 10 is in the shape of a ring defining a central opening 11 and preferably has an open bottom 12. Alternatively, bottom 12 could be closed and instead have a plurality of holes therethrough that would allow fluid to flow out of bottom 12 of main body portion 10.

Sponge 20 is attached to and covers bottom 12. A typical open cell foam may be used for sponge 20.

An anti-microbial agent 15 is carried in main body portion 10 above sponge 20. If desired, anti-microbial agent 15 may be microencapsulated or may be otherwise contained in a rupturable container membrane. Anti-microbial agent 15 may be any anti-microbial that is generally recognized as safe ("GRAS") by the FDA and that substantially inhibits microbial growth on the skin.

When a clinician squeezes or otherwise constricts the area in main body portion 10 above sponge 20, anti-microbial agent 15 flows toward sponge 20. See FIG. 6. Alternatively, if microcapsules or another container for anti-microbial agent 15 is used, the microcapsules or other container holding anti-microbial agent 15 is ruptured. Thereupon, antimicrobial agent 15 flows out of main body portion 10 and into sponge 20 below main body portion 10. Sponge 20 can then be rubbed on the patient's skin to transfer antimicrobial agent 15 to the patient's skin to kill any microorganisms on the patient's skin and sterilize the area.

Located within the central opening 11 of main body portion 10 is plate 30, piston 40 and an anesthetic agent 32 located in rupturable pouch 35 located between plate 30 and piston 40. Plate 30 is preferably formed with a plurality of lumens 31 extending therethrough. In addition, the bottom of plate 30 is preferably formed with a plurality of sharpened points 33 thereon. Alternatively, a micro abrader array could be used with a plurality of holes interspersed therein. In addition, if desired, the top of plate 30 can also be formed with a plurality of sharpened points thereon to facilitate rupture of rupturable pouch 35 for anesthetic agent 32. Plate 30 fits snugly within central opening 11 but is movable axially downwardly therethrough. Plate 30 may be micro-machined from silicon or micromolded from engineering thermoplastic.

Anesthetic agent 32 may be any topically applied anesthetic that is classified as GRAS by the FDA. In order to enhance the permeation of the anesthetic agent through the skin, a permeation enhancer may also be included in rupturable pouch 35 containing anesthetic agent 32. Rupturable pouch 35 may be formed from a low density polymer such as polypropylene.

Piston 40 is located above rupturable pouch 35 and fits snugly within central opening 11 yet is movable axially downward therein. Preferably, piston 40 forms a fluid tight seal with main body portion 10. To achieve this fluid tight seal, piston 40 is formed with a circumferential flange 41 therearound that engages and wipes the inner wall defining central opening 11. Piston 40 is made from a hard material such as polycarbonate to facilitate rupture of rupturable pouch 35 when piston 40 is pushed down against rupturable pouch 35. Preferably, piston 40 has a tapered bottom portion 42 that concentrates the downward force onto a small area on rupturable pouch 35.

Figure 1:
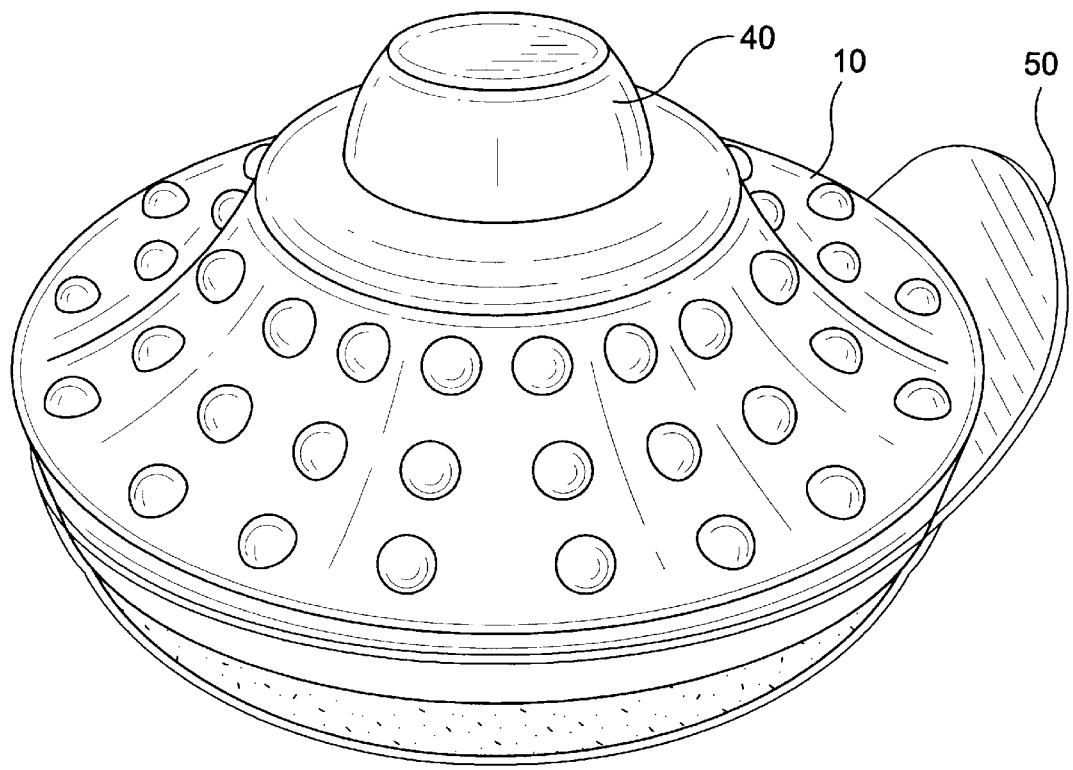
FIG. 1 is a perspective view of the medical site prep device of this invention.
Figure 2:
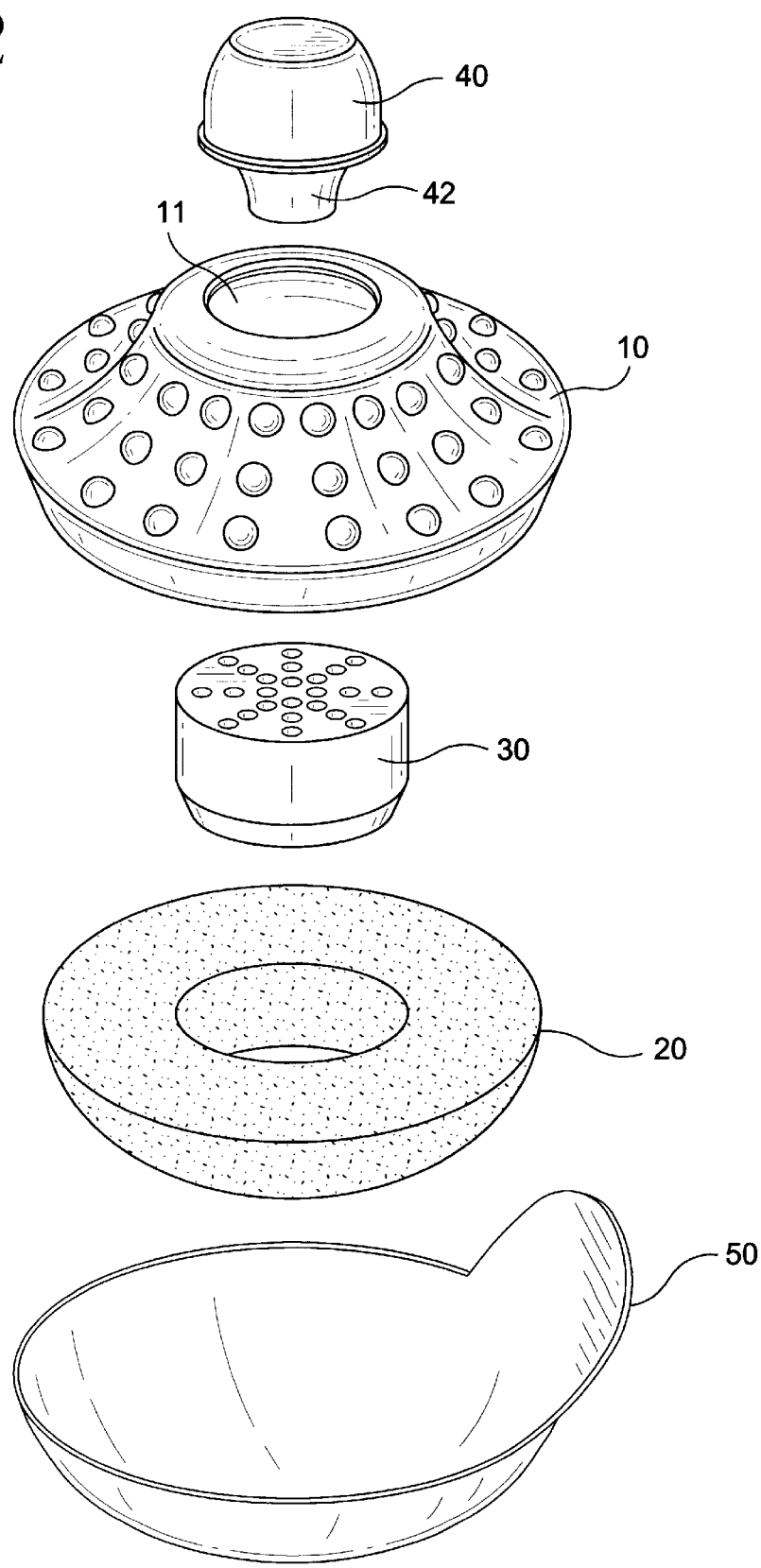
FIG. 2 is an exploded perspective view of the medical site prep device of this invention.
Figure 3:
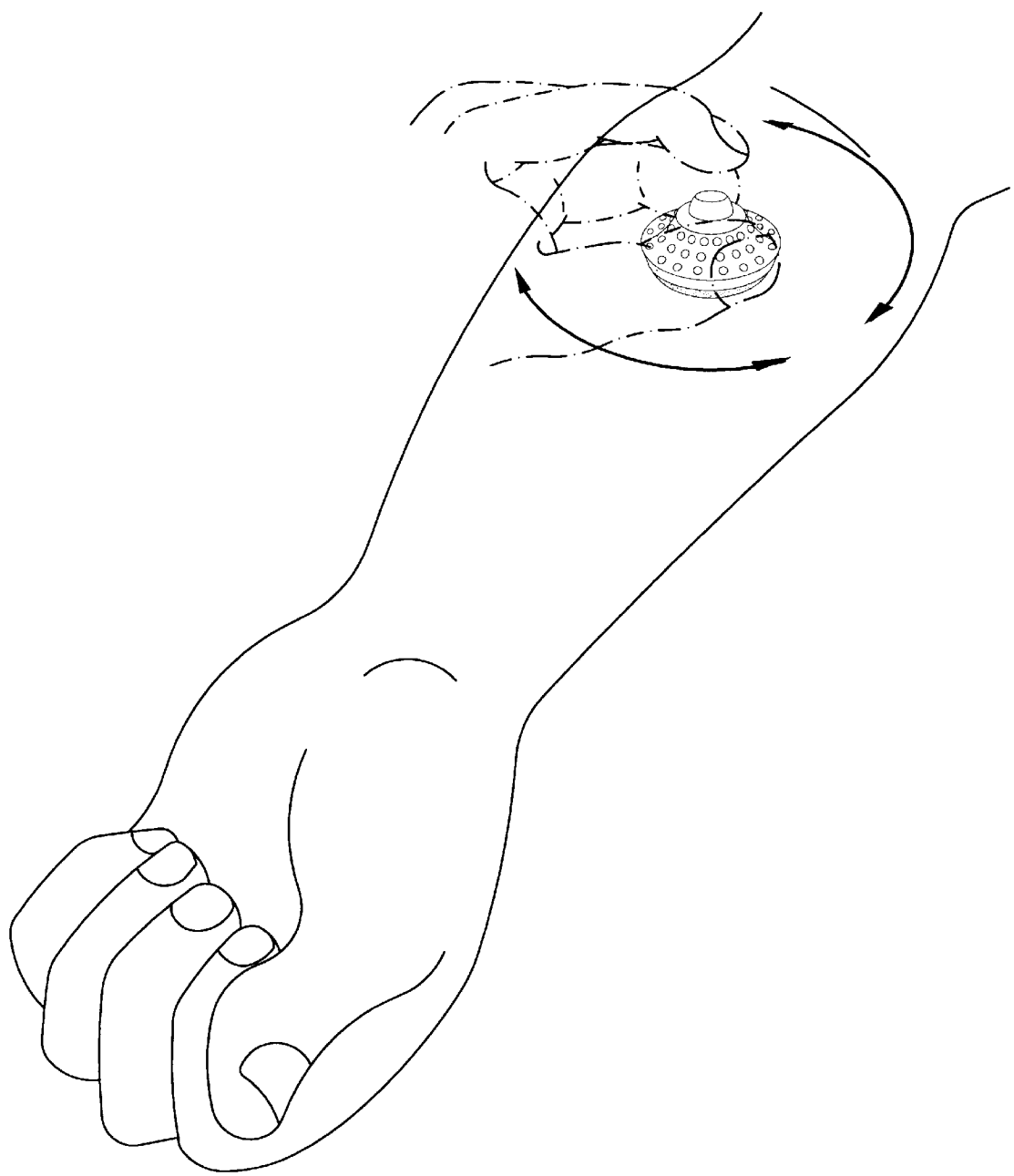
FIG. 3 is a schematic view of a clinician using the medical site prep device of this invention on a patient to dispense the anti-microbial agent.
Figure 4:
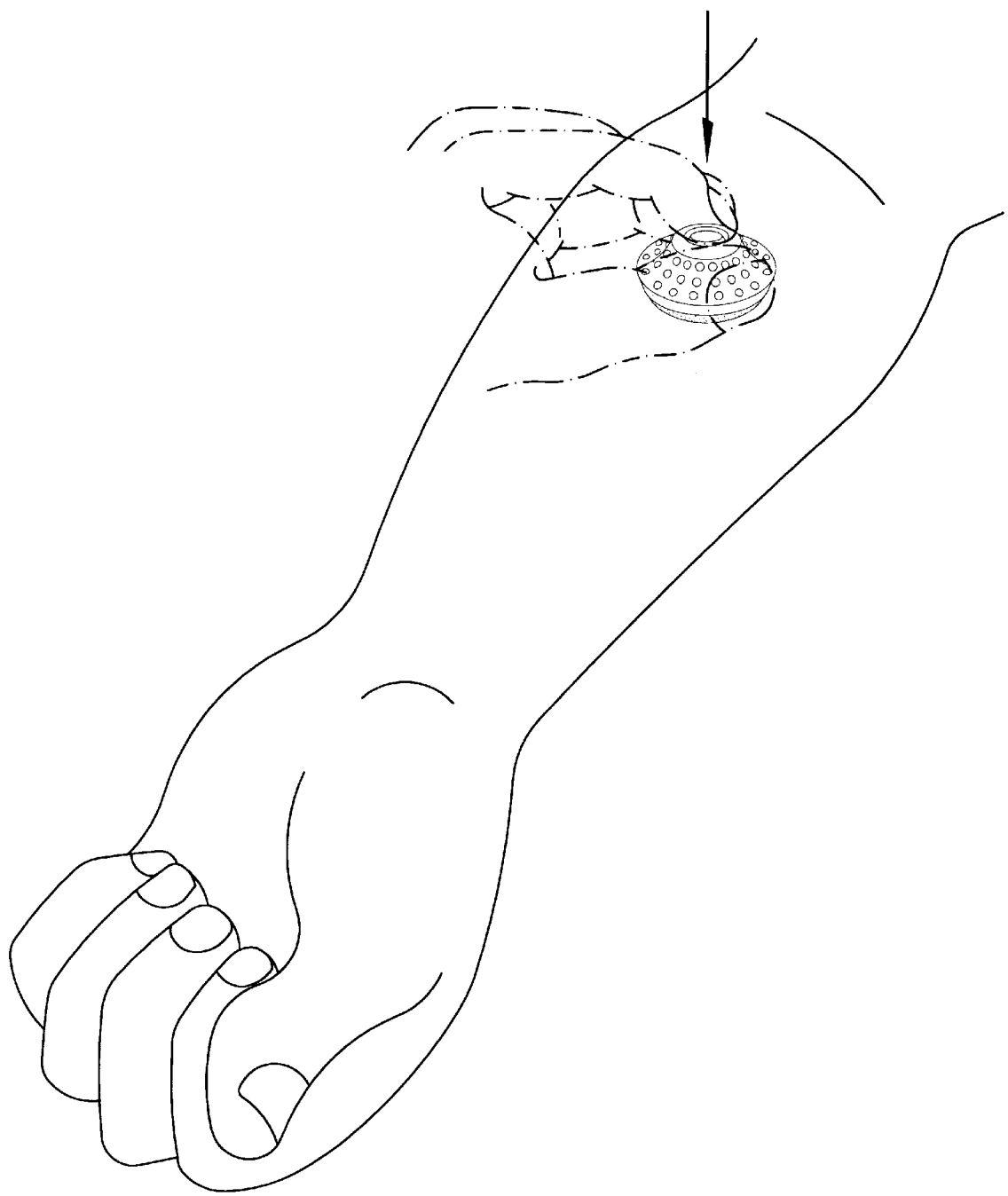
FIG. 4 is a schematic view of a clinician using the medical site prep device of this invention on a patient to dispense the topical anesthetic.

To use the medical site prep device of this invention, the clinician removes film 50 and places the medical site prep device against the patient's skin. The clinician then squeezes main body portion 10 to move antimicrobial agent 15 down into sponge 20. See FIG. 6. Thereupon, antimicrobial agent 15 flows out of main body portion 10 and into sponge 20. The clinician then rubs the medical site prep device, and thus sponge 20 on the patient's skin. See FIG. 3. Thus, any microorganisms on the patient's skin are killed and the area is sterilized. Next, the clinician pushes piston 40 down against rupturable pouch 35 containing topical anesthetic 32. See FIGS. 4 and 7. This motion ruptures pouch 35 so that topical anesthetic 32 flows through lumens 31 onto the patient's skin. In addition, by pushing piston 40 down, plate 30 moves toward the patient's skin so sharpened points 33 abrade the area where topical anesthetic 32 is applied. This enhances the permeation of topical anesthetic 32 through the skin.

Thus it is seen that a medical site prep device is provided that can apply an anti-microbial agent and a topical anesthetic simultaneously to a patient's skin and that is quick and easy to use. The medical site prep device also enhances the permeation through the skin of a topically applied anethestic composition in order to create an anesthetic effect at the site within a short time after application and to a significant distance below the skin.

What is claimed is:

1. A medical site prep device, comprising:

a hollow, main body portion defining a central opening and a bottom area;

an open cell foam connected to the hollow, main body portion adjacent to the bottom area;

a plate defining a plurality of lumens extending therethrough and being disposed in the central opening and wherein the plate has a bottom surface having a plurality of sharp points formed thereon; and a movable piston disposed in the central opening above the plate.

2. The medical site prep device of claim 1 further including a rupturable pouch disposed between the plate and the movable piston.

3. The medical site prep device of claim 1 wherein the plate is movably disposed in the central opening.

4. The medical site prep device of claim 1 wherein the bottom area of the main body portion defines a plurality of holes extending therethrough.

5. The medical site prep device of claim 4 further including a rupturable pouch disposed between the plate and the movable piston.

6. The medical site prep device of claim 5 wherein the plate is movably disposed in the central opening.

\* \* \* \* \*